United States Patent [19]

Smith et al.

[11] Patent Number: 5,736,025
[45] Date of Patent: Apr. 7, 1998

[54] CONTROL OF TEMPERATURE GRADIENTS DURING GEL ELECTROPHORESIS USING TURBULENT GAS FLOW

[75] Inventors: Douglas H. Smith, Los Altos; Brian J. Mifsud, San Francisco; Dean S. Burgi, Menlo Park; Thomas E. Davis, San Francisco; Steven M. VanHuystee, San Mateo, all of Calif.

[73] Assignee: Genomyx Inc., Foster City, Calif.

[21] Appl. No.: 744,689

[22] Filed: Nov. 7, 1996

Related U.S. Application Data

[63] Continuation of Ser. No. 222,583, Apr. 4, 1994, abandoned.

[51] Int. Cl.$^6$ .................................................. C25B 9/00
[52] U.S. Cl. ..................... 204/621; 204/606; 204/616; 34/508; 34/464; 34/611
[58] Field of Search .................................. 204/606, 616, 204/621; 34/508, 464, 611

[56] References Cited

U.S. PATENT DOCUMENTS

| | | | |
|---|---|---|---|
| 1,050,640 | 1/1913 | Sargent. | |
| 3,856,655 | 12/1974 | Roberts | 204/299 |
| 3,905,760 | 9/1975 | Johansson et al. | 432/176 |
| 3,935,646 | 2/1976 | Grandine et al. | 34/92 |
| 4,020,563 | 5/1977 | Hoefer | 34/48 |
| 4,197,657 | 4/1980 | Leino et al. | 34/15 |
| 4,423,391 | 12/1983 | Smith et al. | 34/225 |
| 4,612,106 | 9/1986 | Kromer et al. | 204/299 R |
| 4,612,710 | 9/1986 | Fernwood et al. | 34/16 |
| 4,715,129 | 12/1987 | Uchida | 34/195 |
| 4,750,276 | 6/1988 | Smith et al. | 34/149 |
| 4,757,800 | 7/1988 | Shei et al. | 126/21 |
| 4,883,597 | 11/1989 | Perlman | 210/640 |
| 5,014,512 | 5/1991 | Gombocz et al. | 204/299 |
| 5,053,115 | 10/1991 | Weinberger et al. | 204/299 R |
| 5,060,572 | 10/1991 | Waizmann | 101/424.1 |
| 5,066,382 | 11/1991 | Weinberger et al. | 204/299 R |
| 5,068,176 | 11/1991 | Vijg et al. | 435/6 |
| 5,104,512 | 4/1992 | Gombocz et al. | 204/299 R |
| 5,167,079 | 12/1992 | Bolde et al. | 34/23 |
| 5,560,125 | 10/1996 | Burgi | 34/508 |

FOREIGN PATENT DOCUMENTS

| | | |
|---|---|---|
| 0 455 955 A1 | 11/1991 | European Pat. Off. |
| 2 653 560 A2 | 4/1991 | France. |
| 941 358 | 4/1956 | Germany. |
| 25 08 839 A | 9/1975 | Germany. |
| 94 01 195 | 3/1994 | Germany. |
| 02143145 | 6/1990 | Japan. |
| WO 84/01266 | 4/1984 | WIPO. |
| WO 84/01424 | 4/1984 | WIPO. |

OTHER PUBLICATIONS

Chien and Helmer (1991), "Electroosmotic Properties and Peak Broadening in Field Amplified Capillary Electrophoresis," *American Chemical Society*, vol. 63, pp. 1355–1361.

Garoff and Ansorge (1981), "Improvements of DNA Sequencing Gels," *Analytical Biochemistry*, vol. 115, pp. 450–457.

Product Sheet by Fotodyne Incorporated of New Berlin, Wisconsin (1993).

Product Sheet by Hoefer Scientific Instruments of San Francisco, pp. 79–82, no date given.

(List continued on next page.)

*Primary Examiner*—Cecilia J. Tsang
*Assistant Examiner*—C. Delacroix-Muirheid
*Attorney, Agent, or Firm*—McDonnell Boehnen Hulbert & Berghoff

[57] ABSTRACT

A gel electrophoresis separation apparatus comprising, in combination, a gaseous heat-exchange medium, a gaseous heat-exchange medium driving means, and an impingement means, whereby the gaseous heat-exchange medium is driven by the gaseous heat-exchange medium driving means across the impingement means to provide a flow of the gaseous heat-exchange medium on the surface of the gel plates, whereby the flow induced by passage of the gaseous heat-exchange medium through the impingement means thereby minimizes temperature gradients within the gel by forced convection.

31 Claims, 11 Drawing Sheets

OTHER PUBLICATIONS

BIO-RAD Laboratories, Inc., "The New Power Pac 3000 High Performance Power Supply", Bulletin 1811, no month and date given.

BIO-RAD Laboratories, Inc., "Breakthrough in Mini-Prep Template Preparation! Prep-A-Gene® DNA Mini-prep kit", Bulletin 1810 US REV A, no month and date given.

States et al., 1991, Bio Techniques, vol. 11, No. 1, BioFeedback, "A Gel Electrophoresis System For Resolving Over 500 Nucleotides with a Single Sample Loading", no month and date given.

Sambrook et al., 1988, Molecular Cloning: A Laboratory Manual, 2d ed., Cold Spring Harbor Laboratory Press, Cold Spring Harbor, N.Y., vol. 2, p. 13.46, no month given.

Ausubel et al., 1987 Current Protocols in Molecular Biology, John Wiley & Sons, N.Y., vol. 1, p. 7.6.12, no month given.

Garoff and Ansorge, 1981, Anal. Biochem. 115: 450.

Owl Scientific, Cambridge, Massachusetts "Road Runner™", no month and date given.

Advertisement for Electrophoresis Equipment, Electrophoresis Chambers, no month and date given.

Advertisement in Science, Jan. 7, 1994, vol. 263, by Bio-Rad Laboratories, "Introducing The Hotest News In Sequencing".

BIO-RAD Laboratories, "Hot News for DNA Sequencing", Bulletin 1885 US REV A, no month and date given.

BIO-RAD Laboratories, Inc., "Sequi-Gen® II Nucleic Acid Sequencing System", Bulletin 1746 US, no month and date given.

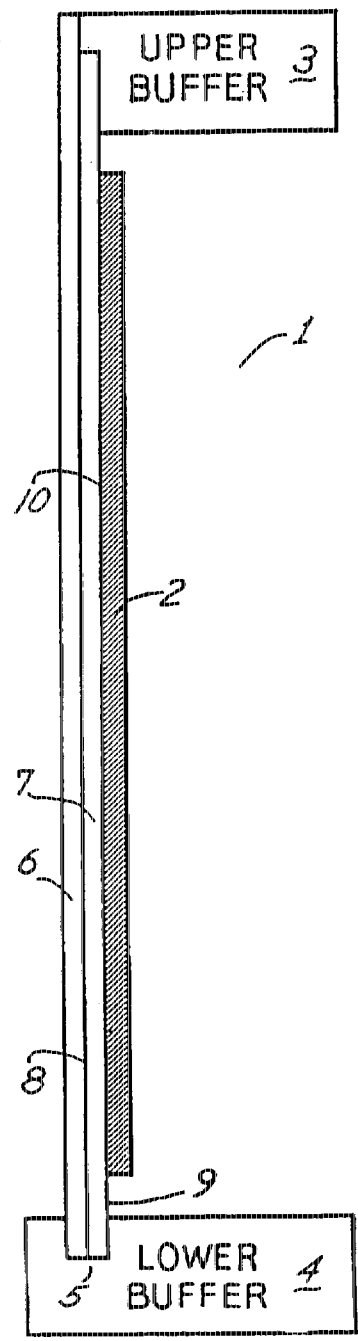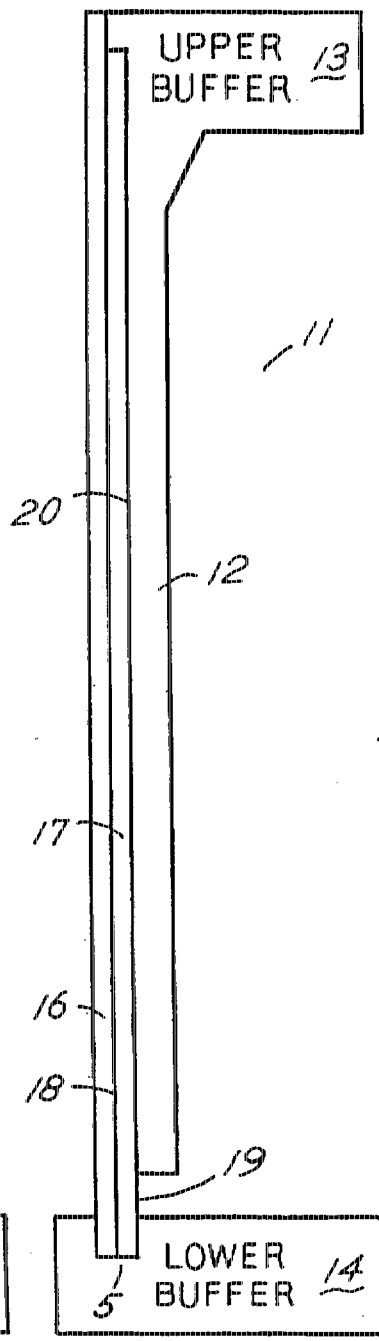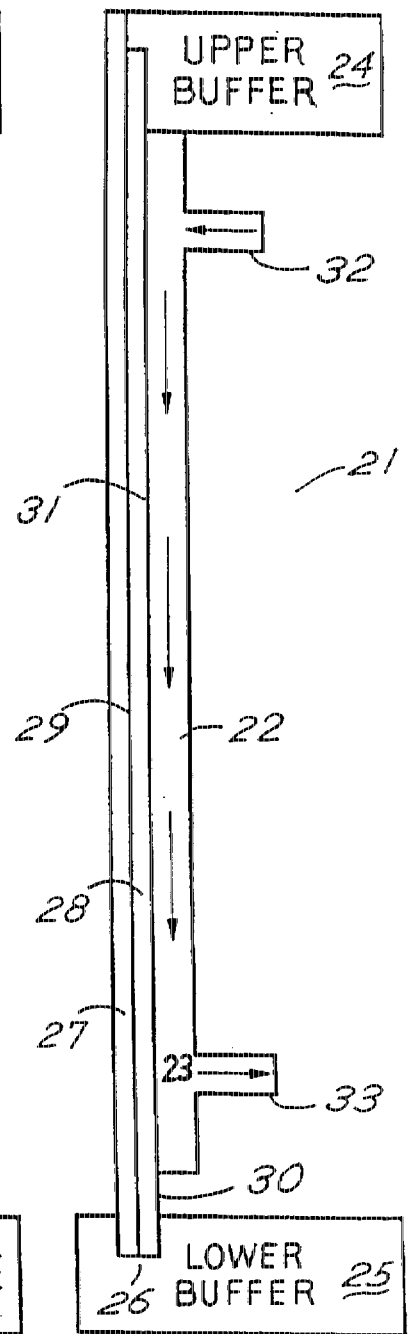

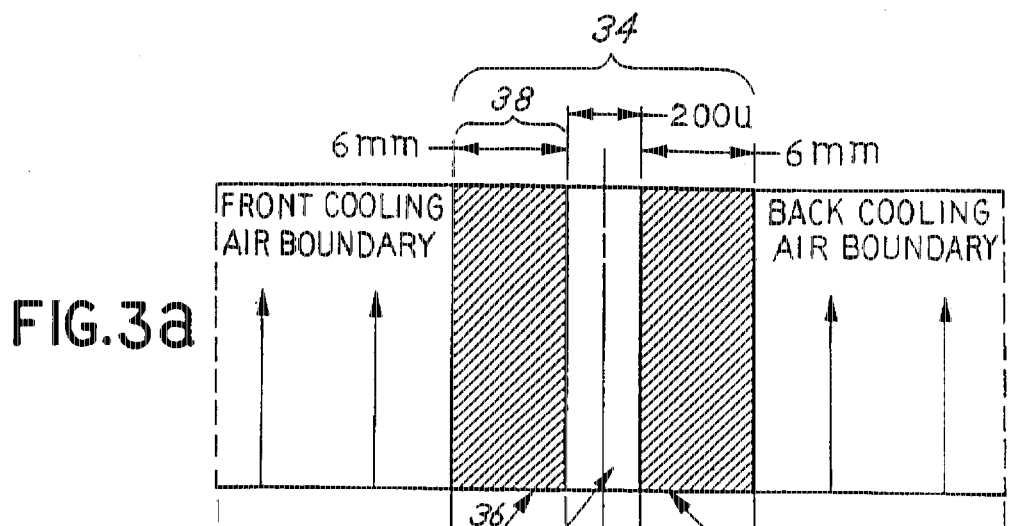
FIG.3a
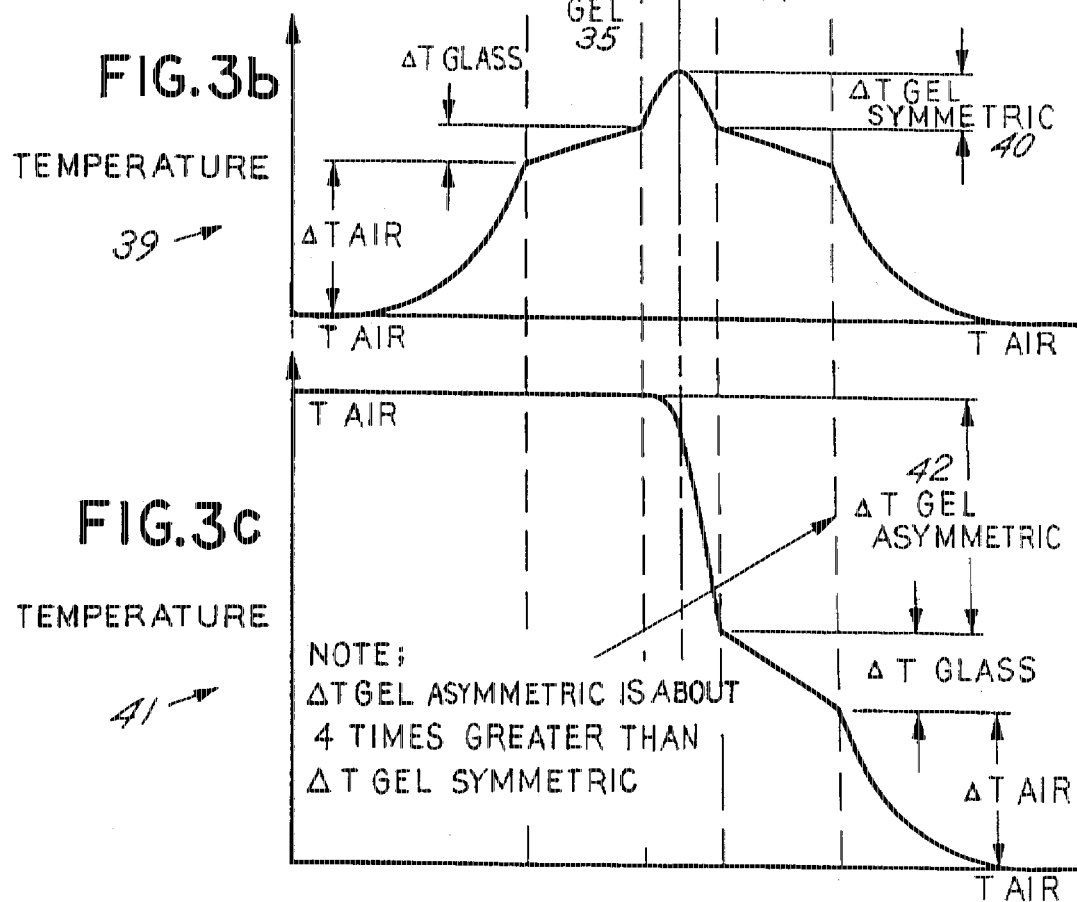
FIG.3b
FIG.3c
NOTE;
ΔT GEL ASYMMETRIC IS ABOUT
4 TIMES GREATER THAN
ΔT GEL SYMMETRIC

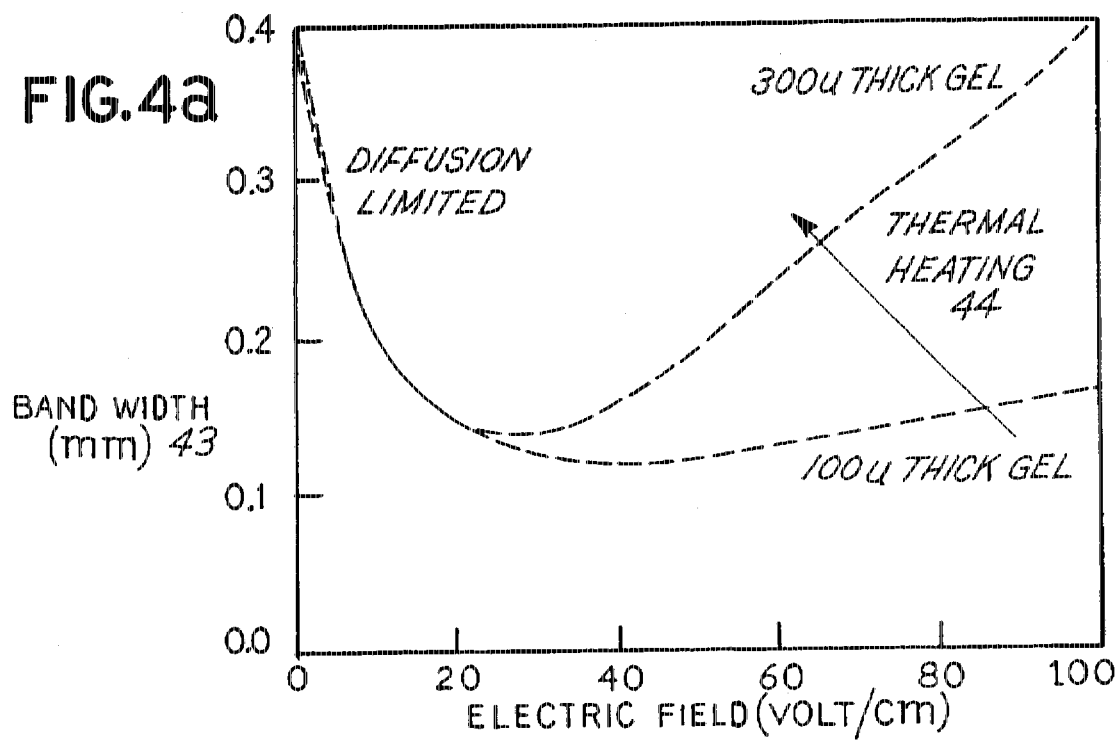
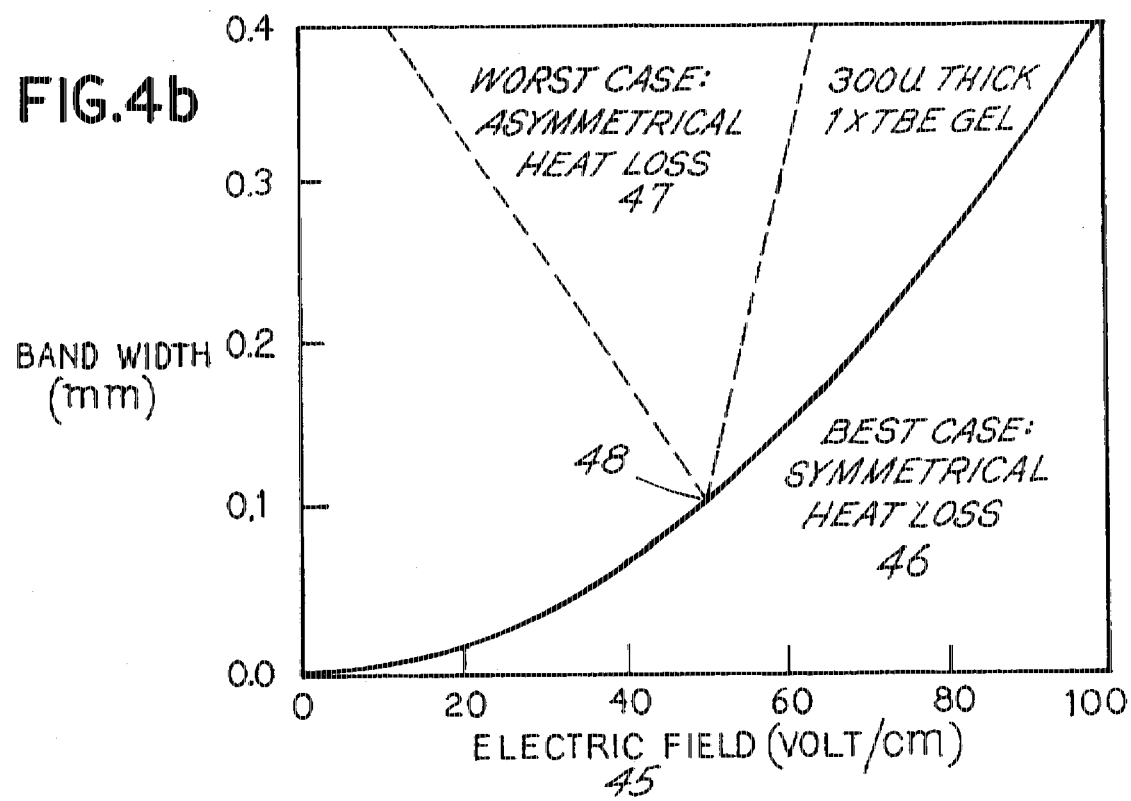

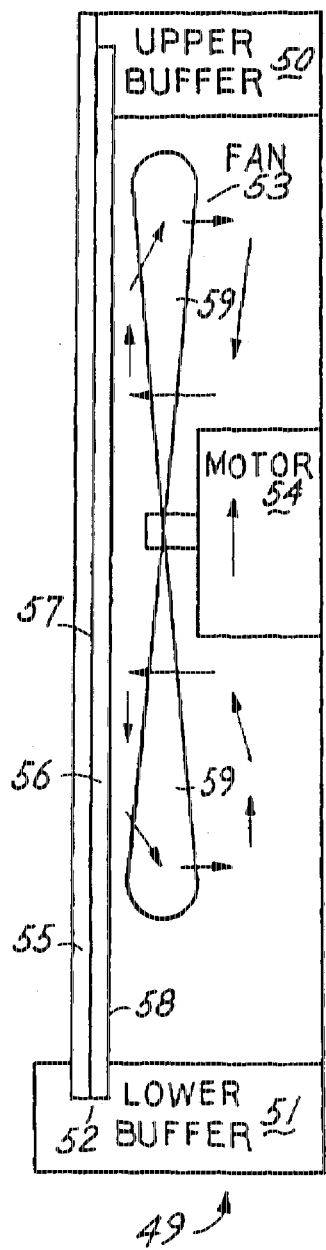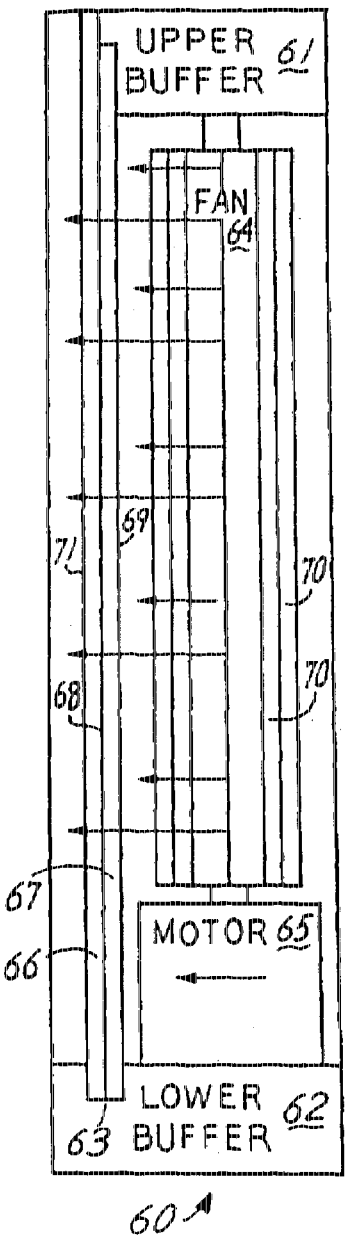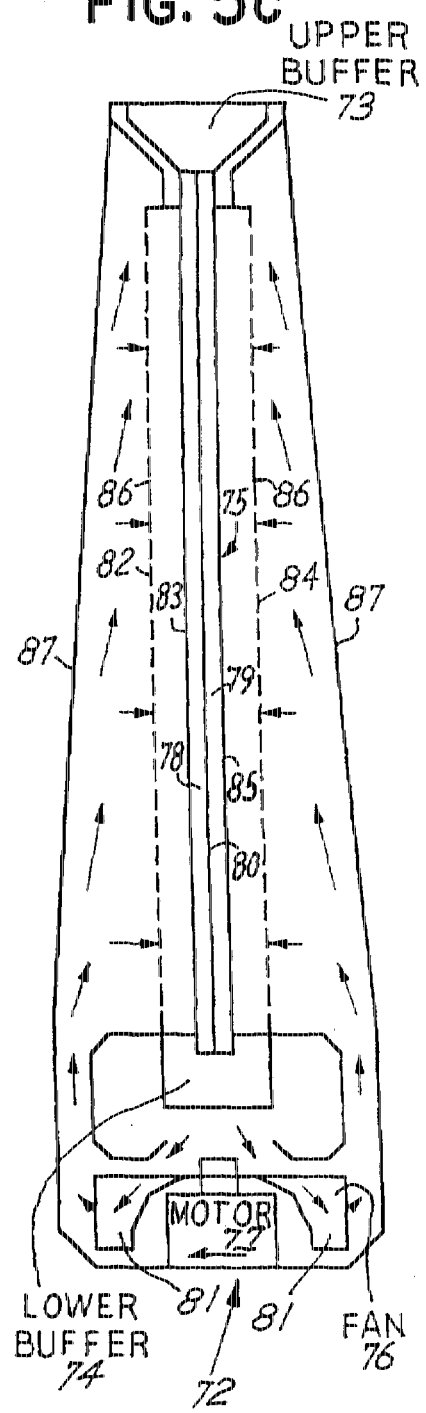

FIG. 6a
FIG. 6b
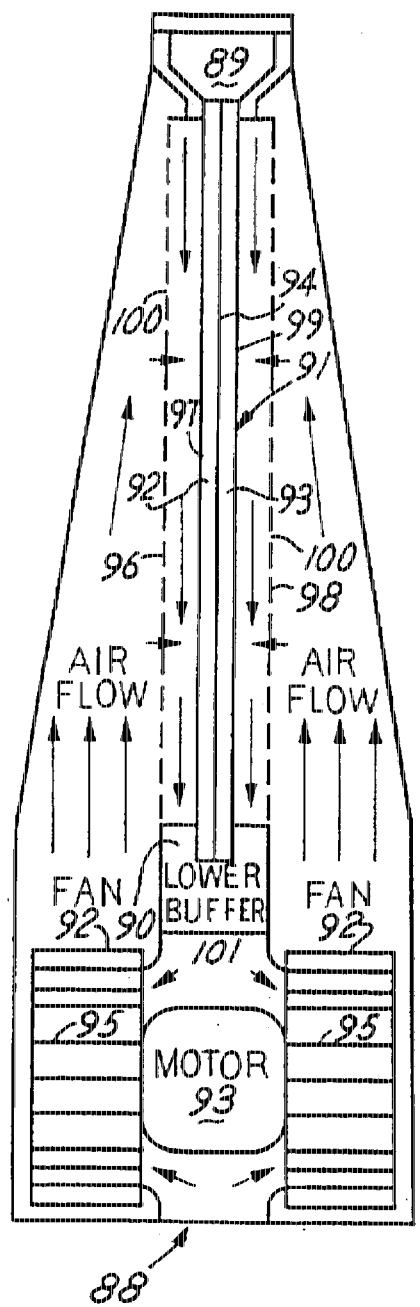
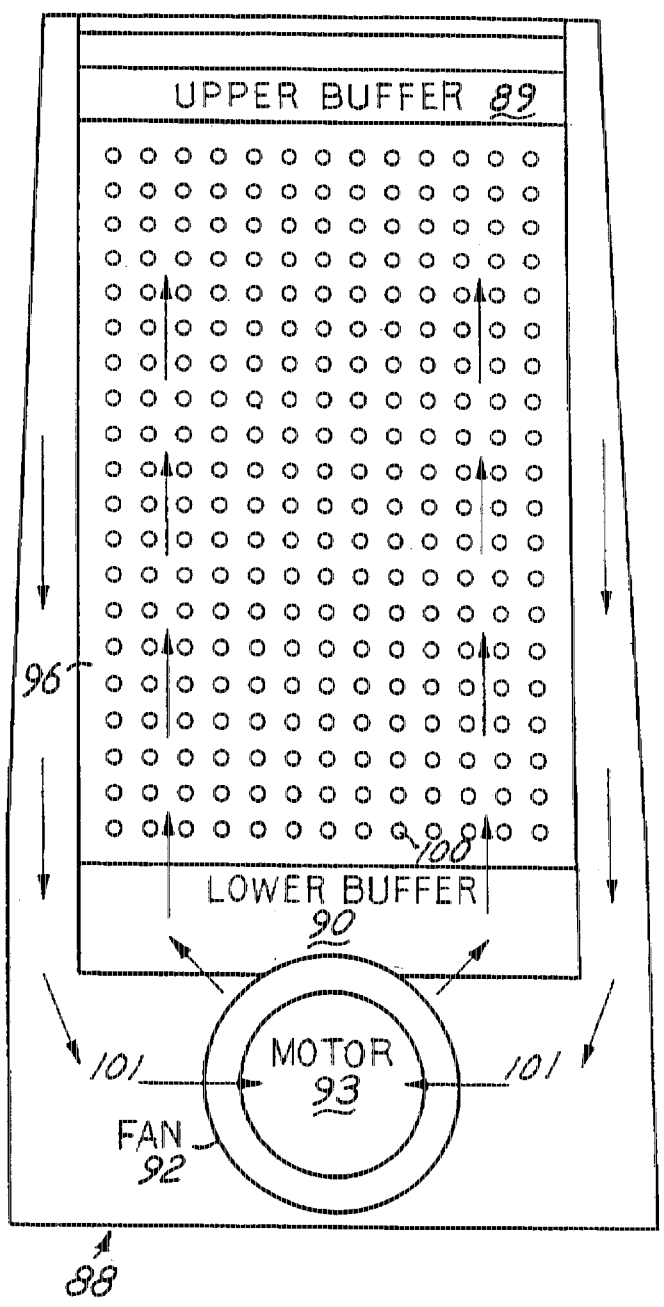

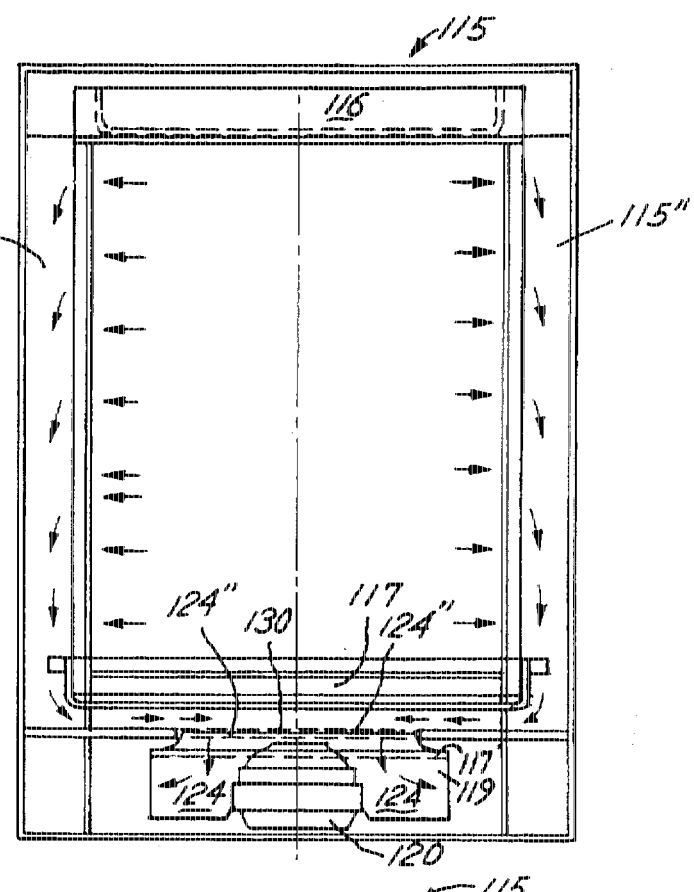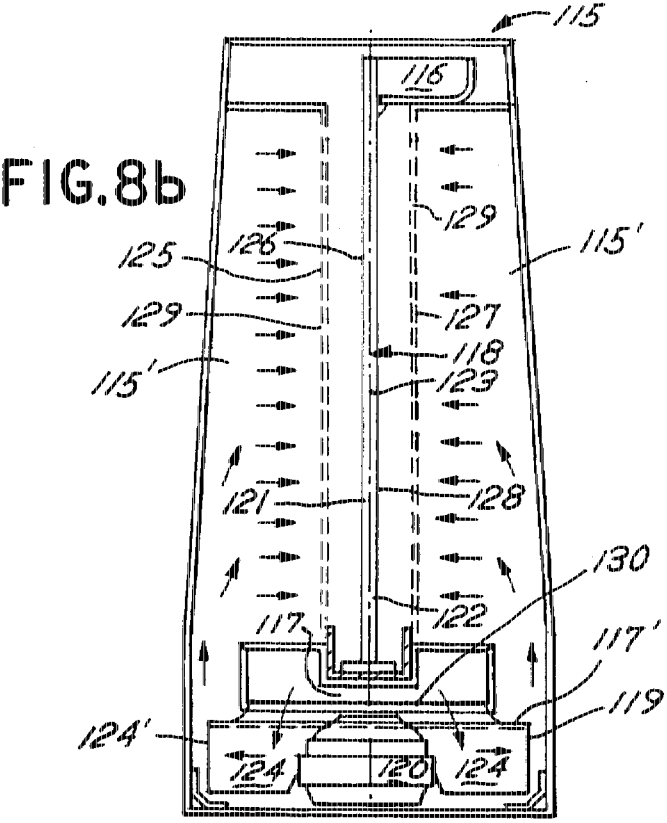

CONTROL OF TEMPERATURE GRADIENTS DURING GEL ELECTROPHORESIS USING TURBULENT GAS FLOW

This application is a continuation of U.S. Ser. No. 08/222,583, filed Apr. 4, 1994, now abandoned.

BACKGROUND OF THE INVENTION

1. Field of the Invention

This invention relates to the separation of single-stranded DNA fragments by slab gel electrophoresis in performing DNA sequencing. Specifically, the invention relates to an apparatus for performing DNA sequence analysis by slab gel electrophoresis wherein the apparatus comprises a turbulent-flow, gas heat-exchange medium impingement-based temperature controlling subassembly. A particular feature of the invention is that thermal temperature gradients generated in the gel separation media during electrophoresis are minimized. The speed, reliability and readability of DNA sequence analysis using the apparatus of the invention is thereby improved.

2. Description of the Prior Art

Gel electrophoresis is a fundamental biochemical separation technique that forms the basis for distinguishing a variety of biologically important molecules on the basis of size, charge or a combination thereof. Specific examples of biological molecules advantageously separated by gel electrophoresis include proteins and nucleic aids. Electrophoresis is usually performed in a gelled (e.g., agarose) or polymerized (e.g., polyacrylamide) media (generically termed a "gel") that contains an electrically conducting buffer. Electrophoresis is performed wherein a voltage is applied via chemically inert metal electrodes across the cross-sectional area of the gel. The biological sample of interest is placed into pre-formed sample wells in the gel, usually at one end of the gel, and the polarity of the applied voltage is arranged so that the biological sample migrates through the gel towards one of the electrodes (usually positioned at the opposite end of the gel from the samples). Where appropriate, the inverse linear relationship between migration distance and molecular size is maintained by the addition of chemical denaturants (such as urea, formamide, or sodium dodecyl sulfate) to the gel and electrophoresis buffer.

A particular application of gel electrophoresis is the separation of single-stranded DNA fragments in the determination of the nucleotide sequence of a nucleic acid of interest. To this end, a collection of single-stranded DNA fragments is generated either by chemical degradation of the nucleic acid (using the Gilbert method, see e.g., Maxam and Gilbert (1980), Methods Enzyme, 65, p499–500) or by replacement DNA synthesis using a polymerase (using the Sanger method, see e.g., Sanger, F., Niklen, S., and Coulson, A. R. (1977) Proc. Nat. Acad. Sci. USA 74, p5463–5467). This collection of single stranded DNA fragments includes a fragment corresponding to each position in the sequence to be determined; in the most frequently-used sequencing method, this correspondence is directly related to the distance from a fixed site of initiation of polymerization at a primer that is annealed to the nucleic acid to be sequenced. Thus, determination of the desired sequence depends on the separation of each of the fragments, which differ in length by only a single nucleotide.

Traditionally, the identity of each of the possible nucleotides at each position (adenine, guanine, cytosine or thymidine) is distinguished by performing a sequencing reaction specific for each ending nucleotide in separate chemical reaction mixtures. Thus, each sequencing experiment is typically performed in 4 separate tubes, wherein are generated a collection of fragments each ending at a position corresponding to the terminating nucleotide used in that reaction. A nucleotide sequence is thereafter determined by performing denaturing gel electrophoresis on each of a set of 4 reactions, each reaction electrophoresed individually in adjacent lanes of a single sequencing gel. The presence of a band at a position in a nucleotide-specific lane of such a gel indicates the identity of that nucleotide at that position in the sequence. Using conventional techniques, each of the fragments is radiolabeled, and the bands are visualized after electrophoresis by autoradiography.

Alternatively, recent technological improvements have resulted in the development of automated sequencing machines. Such machines contain a spectrophotometric detection means at the distal end of the gel opposite to the loading wells. The DNA fragments are synthesized using either a fluorescent-labeled primer or fluorescent-labeled nucleotides. In either case, each of the nucleotide reactions continue to be performed separately, wherein the fragments corresponding to each of the nucleotides is fluorescently labeled with a distinguishable fluorescent label. However, because each fluorescent label exhibits fluorescent emission at a characteristic frequency, it is possible to distinguish the identity of the nucleotide at the terminal position of each fragment from its fluorescence emission signature. This feature allows the automated collection of nucleotide sequence information spectrophotometrically using these devices. In addition, the existence of distinguishable fluorescent signatures for each of the fragments allows the products of the four separate sequencing reactions to be electrophoresed in a single lane of the gel.

These developments have increased the requirements for accurate and reliable separation of the sequencing fragments generated in nucleotide sequencing reactions. However, there are a number of technical limitations inherent in current slab gel electrophoresis technology that have remain unsolved in the current state of this art. For example, limitations on the range of distinguishably-separable fragments necessitates that each sequencing reaction series be loaded onto the gel in two sets of lanes loaded at two separate times. The lanes loaded first (and thus electrophoresed longest) are used to determine the nucleotide sequence furthest from the polymerization initiation site (and are thus the longest fragments), while the second-loaded set are read to determine the nucleotide sequence closest to the initiation site. The relative timing of loading and the time the reactions are allowed to electrophorese are empirically chosen so that these ranges overlap; thus, one entire section of any particular nucleotide sequence can be read. The result of these limits of this electrophoresis is that a maximum of 350–400 bases can be read from a sequencing reaction that is initiated at a given site. Thus, the development of methods and apparatus capable of resolving a longer extent of nucleotide sequence than is currently possible would be a useful development in this art.

A number of other technical constraints that limit the extent of nucleotide sequence information that can be obtained using conventional electrophoresis techniques are the consequence of the electrophoretic conditions needed for DNA sequence analysis using slab gel electrophoresis. Pre-eminent among these are thermal temperature gradients produced within the gel during electrophoresis.

In order to separate the single-stranded DNA fragments during electrophoresis proportional to the length of each fragment, a potential of 1000–3000 volts ((1–3 kilovolts (kV)) is typically applied across the gel for 2–16 hours. Approximately 30 to 60 watts of power is dissipated uniformly in the gel as heat and then from the surface of the gel plates containing the slab gel. Such heating is useful (and, in fact, necessary), because it promotes maintenance of the single-stranded DNA in the denatured state (so that migration distance is inversely proportional to fragment length). However, the extent of such heating is limited to the thermal tolerance of the materials comprising the electrophoresis apparatus. This limitation places an upper limit on the magnitude of the applied voltage; since the duration of electrophoresis depends on the magnitude of the applied voltage, the capacity for decreasing the duration of electrophoresis is also constrained by the limitation of the magnitude of the applied power.

An additional problem associated with electrogenic heating of DNA sequencing gels is the uneven distribution of such heat throughout the gel, resulting in thermal temperature gradients in the gel. Under conventional denaturing acrylamide gel electrophoresis conditions, the central one-quarter to one-third of the gel becomes warmer during electrophoresis than the rest of the gel throughout its length. Because the mobility of the single stranded DNA fragments varies proportionally with temperature (at an increasing rate of approximately 2.2% per °C.), the consequence of uneven heating is that the samples in the center lanes run faster than the samples on the edges. The result is the production of sequencing gels wherein the pattern of bands in the lanes across the gel gives the appearance of "smiling": the bands are progressively shifted anodally (i.e. upwards using conventional techniques) going from the center of the gel towards the edges.

Another serious problem to which there was no solution proposed or implemented in the prior art is the problem associated with high-voltage slab gel electrophoresis—the generation of front-to-back thermal temperature gradients. In particular, the resolution of each of the bands from all other bands resolved in each lane of a sequencing gel is affected by these types of thermal gradients.

Band resolution depends on the size (i.e., the thickness) of each band, as well as the relationship between the average thickness of each band and the width of the space separating each band. A sequencing ladder comprised of thick bands will contain fewer resolvable bands on average than a gel having thinner, more tightly-resolved bands, simply due to the finite length of the resolvable portion of the gel. Also, since each of the bands in a sequencing gel can in principle be separated by as few as one nucleotide, stretches of DNA having multiple repeats of a particular nucleotide (e.g., 5'-TTTTTTTTT-3') will be more difficult (if not impossible) to resolve in a gel having thicker, less tightly-resolved bands than in a gel having thinner, more tightly-resolved bands. Although this factor is particularly important for resolving repetitive stretches of one type of nucleotide (because the phenomenon is exacerbated by electrophoresis in the same lane of single-stranded DNA fragments corresponding to each of these nucleotides), the problems of band resolution that are band width-related also occur in certain portions of a gel across more than one gel lane (so-called "compression zones").

These problems have been recognized in the prior art, as is evidenced by the use of [$^{35}$S]-labeled deoxynucleotides for labeling the DNA in sequencing reactions (see Sambrook et al., vide infra). The bandwidths of autoradiographic bands produced from β-particle emissions from $^{35}$S are narrower than the bandwidths produced from $^{32}$P β-particle emissions because $^{35}$S emits lower-energy particles that convert silver grains over a narrower area in the autoradiographic film. The usefulness of such narrower bandwidths is evidenced by the acceptance of this method in the art in the face of a number of practical disadvantages associated with $^{35}$S use. These include longer autoradiographic development times.

A major determinant of the band-width of single-stranded DNA fragments separated by slab gel electrophoresis using high voltages is the generation of front-to-back thermal temperature gradients in the gels during high-voltage electrophoresis. Thus, there was an unappreciated and unfulfilled need in the DNA sequencing/gel electrophoresis art for an apparatus for performing high-voltage, slab gel electrophoresis under conditions in which both front-to-back as well as side-to-side thermal temperature gradients are minimized.

Thus, limitations of the prior art include: limits on how high the voltage can be, due to overheating of the gels and thereby resulting in longer run times; limits on ionic strength since higher ionic strengths need higher power; and uneven heating, causing "smiling" (i.e., left-to-right) distortion and decreased resolution (front-to-back).

Attempts to minimize these types of such thermal gradients are known in the prior art, and in general comprise three related approaches.

1. Aluminum-Backed Plate

The aluminum-backed plate is described in general molecular biology reference manuals of best practices with no reference to an originator (see Sambrook et al., 1988, *Molecular Cloning: A Laboratory Manual*, 2d ed., Cold Spring Harbor Laboratory Press, Cold Spring Harbor, N.Y., vol. 2, p13.46, and Ausubel et al., 1987, *Current Protocols in Molecular Biology*, John Wiley & Sons, N.Y., vol. 1, p7.6.12).

In conventional (usually home-made) embodiments of this type of electrophoresis apparatus, an aluminum plate is clamped to the front or back glass plate containing the gel as a means of evening out the temperature gradient. However, heat transfer between the glass plate and the aluminum plate is somewhat variable because of non-uniform flatness of the contacting surfaces and the poor thermal conductivity of air. Using aluminum-backed plate devices, the side-to-side temperature gradients produced in the gels under conventional conditions of denaturing slab gel electrophoresis are reduced by 1° to 3° C. The "smiling" artifact is reduced substantially using this apparatus, but is nevertheless still detectable and poses a hindrance to easy determination of a nucleotide sequence arrayed within the gel.

2. Buffer-Backed Plate

The buffer-backed plate type of apparatus (commercially available from Bethesda Research Labs, Gaithersburg, Md. and BioRad, Hercules, Calif.) is also described in general molecular reference manuals of best practices with no reference to an originator (see Sambrook et al., ibid.). The buffer-backed plate is somewhat more effective than the aluminum-backed plate because of the more uniform heat transfer between a free convection fluid (buffer) and the glass plate. As a result, this system reduces "smiling" to an acceptable level for manual reading; however, the construction of the sequencing gel apparatus is complicated by the requirement for a water tight sealed compartment that extends the full length of the back plate.

3. Circulating Water

Further improvement in the buffer-backed plate type of apparatus has been obtained by using forced convection of a fluid (usually water) on the back side of the glass, as described by Caroff and Ansorge, (1981, Anal. Biochem.

115: 450) and commercially-available from Pharmacia, Milwaukee, Wis. This embodiment achieves a very uniform temperature distribution from side to side and yields a pattern of straight bands in lanes substantially across the width of the gel. This embodiment has been used successfully in conjunction with automated gel sequence readers using stationary photodiode tubes, as described above. However, this embodiment suffers from the disadvantage that a special circulator pump is required; this pump supplies both suction and pressure regulated to avoid high pressures inside the jacket which could break the glass-to-plastic water jacket seal during operation. This disadvantageously adds to the cost of such a system. An additional disadvantage is the presence of water in the circulating jacket in proximity to the high voltages associated with DNA sequencing by slab gel electrophoresis.

4. Laminar-flow Air-cooled Capillary Electrophoresis

Weinberger, U.S. Pat. No. 5,053,115, issued on Oct. 1, 1991, describes a capillary electrophoresis apparatus wherein the temperature of the gel is kept constant using a laminar-flow air-cooled jacket or manifold fitted around the outside of the capillary tube. In this device, a heating element is placed on one side of a capillary tube and a fan on the other side, and heat-sensing elements used to maintain a constant temperature across the surface of the capillary tube by laminar air flow.

Owl Scientific, Cambridge, Mass. has marketed a slab gel electrophoresis device (called the "Road Runner™") that uses the flow of compressed air, such as is commonly found at the benchtop in scientific laboratories, over slab gels to cool such gels during electrophoresis by convection. Air warmed by convective heat transfer from the gel plates is vented from the apparatus to effect heat withdrawal from the system. Notched aluminum plates are also available to enhance the convective cooling provided by the apparatus.

SUMMARY OF THE INVENTION

This invention relates to the use of forced air temperature control of gel electrophoresis separations. In particular, this invention relates to forced air methods and apparatus for accurately controlling the side-to-side and more importantly the front-to-back thermal gradients in slab gels to improve the read length of DNA sequences.

In particular, this invention discloses the use of several split flow methods that provide symmetrical heat transfer to both sides of the glass gel plates resulting in lower front-to-back gradients in the gel and a corresponding improvement in the resolution of separated DNA fragments.

A further improvement is obtained using split flow air impingement on the front and back glass surfaces. The invention is useful in determining DNA sequences by slab gel electrophoresis and in particular the reading of DNA sequences to much longer lengths than is the present practice.

Major contributions of this invention to the art include a number of unique ways to achieve balanced temperature gradients in the gel, including: balanced front-to-back temperature gradients in the gel to extend resolution of separated DNA fragments; balanced side-to-side temperature gradients in the gel to reduce "smiling" type distortion; and balanced top-to-bottom temperature gradients in the gel to achieve repeatable run times.

The advantages over prior art apparatus includes the ability to run the gels at high and uniform temperatures so that the DNA remains denatured. Another advantage of the present invention is the ability to use low ionic strength buffers to extend the readability of the runs. The present invention also provides the ability to use higher voltages (and therefore higher power/wattage) to increase the speed of extended runs. Still another advantage of the present invention is that it provides symmetrical turbulent airflow over the gel plates, thereby minimizing front-to-back and side-to-side thermal gradients. Other advantages of the present invention include high heat transfer coefficients and the ability to maintain constant thermal conditions at greater or less than ambient temperatures.

The present invention has the ability to decouple the gel temperature from the power dissipation in the gel, allowing optimized conditions.

BRIEF DESCRIPTION OF THE DRAWINGS

FIGS. 1a and 1c show band patterns using conventional methods and FIGS. 1b and 1d show band patterns using the apparatus of the present invention.

FIGS. 2a, 2b and 2c represent conventional apparatus for reducing temperature gradients during slab gel electrophoresis.

FIGS. 3a, 3b and 3c are graphic representations of the temperature profile of a gel layer between air-cooled glass plates.

FIGS. 4a and 4b illustrate the extent of thermal contribution to DNA band width.

FIGS. 5a, 5b and 5c illustrate embodiments of the present invention having forced-air methods for reducing temperature gradients.

FIGS. 6a and 6b show an embodiment of the present invention having a turbulent-flow, two sided jet impingement apparatus having two scroll fans powered by a single motor drive.

FIGS. 8a and 8b show another embodiment of the present invention having a double-sided tangential-fan system having a single fan at the bottom of the apparatus.

DETAILED DESCRIPTION OF THE PREFERRED EMBODIMENTS

Figure 1A:
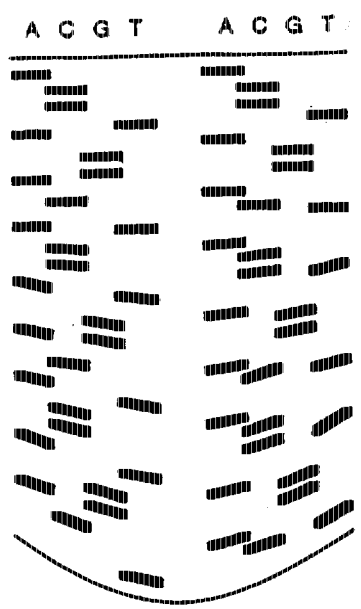
FIGS. 1a through 1d illustrate distortions caused by temperature gradients in slab gels after high-voltage electrophoresis.
Figure 1B:
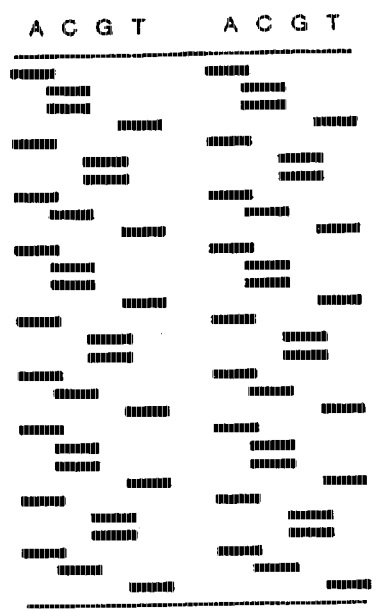
Figure 1C:
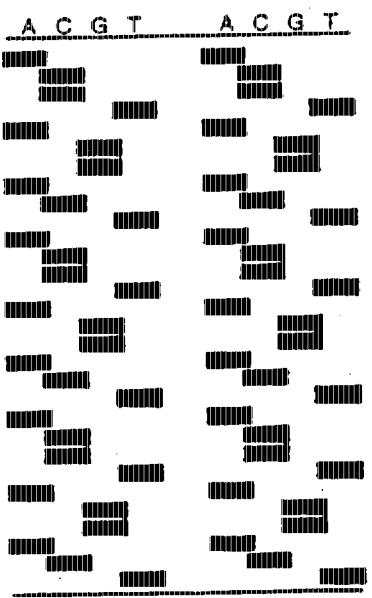
Figure 1D:
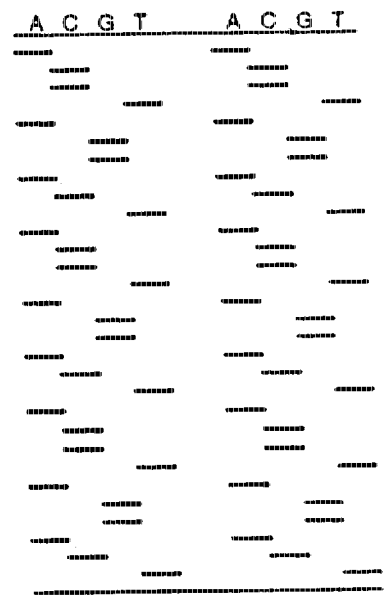

FIGS. 1a through 1d illustrate distortions caused by temperature gradients in slab gels after high-voltage electrophoresis. FIGS. 1a and 1c show single-stranded DNA fragment band patterns produced using conventional methods. FIGS. 1b and 1d show identical patterns produced using the apparatus according to the present invention, i.e. the embodiment shown in FIGS. 6, 7 and 8.

More specifically, FIG. 1a shows the severe distortion in single-stranded DNA fragment band patterns referred to as "smiling" caused by high side-to-side thermal gradients. FIG. 1b shows the same pattern of DNA fragment bands when such side-to-side thermal gradients are reduced using the present invention.

FIG. 1c shows the wider bands caused by spreading due to high front-to-back thermal gradients. FIG. 1d shows the thinner band-widths found in gels in which front-to-back thermal gradients have been reduced using the present invention. A comparison of the resolution of the bands shown in each of FIGS. 1c and 1d illustrates the shorter extent of nucleotide sequence readability caused by high front-to-back thermal gradients.

FIGS. 2a, 2b and 2c represent conventional apparatus for reducing temperature gradients during slab gel electrophoresis. In FIG. 2a, an apparatus 1 has an aluminum backing plate 2, an upper buffer 3, a lower buffer 4, and a glass gel slab 5. Glass gel slab 5 is comprised of a front glass plate 6 and a back glass plate 7 that are substantially parallel to each other and between them, contain gel 8. In this embodiment, the aluminum backing plate 2 is clamped to the back 9 of back glass plate 7 to form an interface 10.

In FIG. 2b, an apparatus 11 has a buffer backed plate 12, an upper buffer 13, a lower buffer 14, and a glass gel slab 15. Glass gel slab 15 is comprised of a front glass plate 16 and a back glass plate 17 that are substantially parallel to each other and between them, contain gel 18. In this embodiment, the buffer backed plate 12 is clamped to the back 19 of back glass plate 17 to form an interface 20.

In FIG. 2c, an apparatus 21 has a circulating water plate 22 having circulating water 23, an upper buffer 24, a lower buffer 25, and a glass gel slab 26. Glass gel slab 26 is comprised of a front glass plate 27 and a back glass plate 28 that are substantially parallel to each other and between them, contain gel 29. In this embodiment, circulating water plate 22 is clamped to the back 30 of back glass plate 28 to form an interface 31. Circulating water 23 enters at entry port 32 and flows through circulating water plate 22 and exits through exit port 33. In this embodiment, circulating water 23 carries away heat from glass gel slab 26 and is then cooled and recirculated by conventional methods which are not shown.

FIGS. 3a, 3b and 3c are graphic representations of the temperature profile of a gel layer between air-cooled glass plates. More specifically, FIG. 3a shows the cross-section 34 of gel 35 formed between a front glass plate 36 and back glass plate 37 of approximately equal thickness 38; FIG. 3b shows the temperature profile 39 in gel 35 under conditions of symmetrical heat transfer to the surrounding air; under these conditions, the temperature gradients in the gel 35 are symmetrical, and this results in the lowest peak parabolic temperature gradient in the gel 35 (ΔTgel 40), and the lowest amount of extra band spreading; FIG. 3c shows the temperature profile 41 in the gel 35 under conditions of asymmetrical heat transfer to the surrounding air; under these conditions, the temperature gradients in the gel 35 are asymmetrical and more heat is transferred to one side of the gel 35 than the other, resulting in a front-to-back thermal temperature gradient (ΔTgel 42); this pattern is found in the configurations of gel electrophoresis apparatus such as the apparatus 1 having aluminum backed plate 2 of FIG. 2a, the apparatus 11 having buffer backed plate 12 of FIG. 2b, and the apparatus 21 having circulating water plate 22 of FIG. 2c. Comparison of the ΔTgel values shown in FIGS. 3b and 3c reveals a much larger (approximately four-fold) temperature gradient in the gel 35 under asymmetric conditions, resulting in a substantial degradation in band spreading and loss of resolution.

The 200μ thin gel is formed between two roughly equal thickness glass plates. The polyacrylamide gel is typically made with 1×TBE buffer and is conductive. With several thousand volts applied across the length of the gel, approximately 40 watts of power is uniformly generated in the gel.

If the heat transfer is balanced on both sides of the gel, the temperature gradients are symmetrical resulting in the lowest peak parabolic temperature gradient in the gel, ΔTgel, and the lowest amount of extra band spreading. For typical operating conditions, the gradient in the gel is on the order of 0.03° C. and the mobility of DNA in the gel has a temperature coefficient of 2.3%/°C. resulting in band spreading of a fraction of a mm over a 20 cm length of the gel.

In the typical case, more heat is conducted toward the aluminum or buffer backed plate than the other side of the system that is exposed to free air having poor heat transfer. The system in the worst case would have all of the heat conducted out the back resulting in a much larger temperature gradient in the gel, ΔTgel, and a substantial degradation in band spreading and loss of resolution. Under these conditions, the temperature gradient in the gel will be four times as great resulting in a corresponding loss of resolution of four times.

FIGS. 4a and 4b illustrate the extent of thermal contribution to DNA band width. Specifically, FIG. 4a shows the opposed effects on band-width of diffusion 43 and thermal heating 44 for a 100μ thick gel and a 300μ thick gel relative to the electric filed strength 45 in each gel. This plot shows the expected band width as a function of the electric field (power dissipation in the gel). At very low fields (low power levels), the band width is limited by diffusion of the slow moving DNA fragments in the gel matrix. At higher fields (faster runs) the band width is determined by the parabolic thermal profile in the gel since it causes a non-uniform migration of fragments. Thicker gels have a higher parabolic thermal profile and thus wider band widths for a given field. The trend is to thinner gels for faster high resolution runs, but thinner gels are more difficult to handle and have lower sample loading capacity.

FIG. 4b shows the effects of thermal heating in a 300μ-thick gel prepared with 1X Tris-borate-EDTA buffer in the best case (i.e., symmetrical heat loss 46) and the worst case (i.e., asymmetrical heat loss 47); the two curves intersect at the point 48 where the electric field strength 45 is about 50 volts/cm.

The solid line shows the thermal spreading effect for a 300μ thick gel with a symmetric thermal gradient in the gel (equal heat loss out the front and back surface of the glass plates). If the system is set up such that the heat loss from the front surface varies, performance is found to track the dashed line. At one point, the heat loss is exactly balanced out the front and back corresponding to where the dashed lines meet the solid symmetric case line. If the heat flow is not balanced, then one is operating up on one of the dashed lines with radically increased band widths. Conventional DNA gel fixtures attempt to operate near the symmetric point by adjusting the heat losses and power levels. However, this point is not stable and depends on the free convection to the room air, contact resistance of the back aluminum plate and many other thermal variables that are difficult to predict or control.

FIGS. 5a, 5b and 5c illustrate embodiments of the present invention having forced-air methods for reducing temperature gradients. Air flow is shown with arrows. In FIG. 5a, turbulent flow one side plate apparatus 49 has an upper buffer 50, a lower buffer 51, a glass gel slab 52, and a fan 53 that is driven by motor 54. Glass gel slab 52 is comprised of a front glass plate 55 and a back glass plate 56 which are substantially parallel to each other and between them, contain gel 57. Fan 53 is positioned so that it faces the back 58 of back glass plate 56. Further, fan 53 has propeller blades 59. Fan 53 circulates air on back 58 of back glass plate 56. Thus, apparatus 49 is constructed with a large mixed flow impeller fan 53 placed near the back glass plate 56 and thus, turbulent air is circulated over primarily one side of glass gel slab 52, i.e., back 58 of back glass plate 56. This approach performs as well as the buffer backed example shown before in controlling side-to-side gradients. No attempt was made to circulate high velocity air on both sides of the front and back glass plate, and thus the thermal gradients were asymmetric front-to-back and suffered the same resolution losses as the other conventional units.

In FIG. 5b, a laminar flow two sided plate apparatus 60 has an upper buffer 61, a lower buffer 62, a glass gel slab 63, and a fan 64 that is driven by motor 65. Glass gel slab 63 is comprised of a front glass plate 66 and a back glass plate 67 which are substantially parallel to each other and between them, contain gel 68. Fan 64 is positioned so that it faces the back 69 of back glass plate 67. Further, fan 64 has blades 70 that extend vertically and are between upper buffer 61 and lower buffer 62. Air is circulated by fan 64 in a laminar flow manner for both back 69 of back glass plate 67 and the front 71 of front glass plate 66. This apparatus is made with a conventional long squirrel-caged blower fan 64 that is mounted to a side of the glass gel plates 66 and 67. Fan 64 circulates air and the air is flow split so that substantially half is passed over the front 71 of front glass plate 66 and substantially half over back 69 of the back glass plate 67, thereby eliminating most of the front-to-back gradients. Front-to-back gradients across the glass plates 66 and 67 measured with thermocouples were 0.3°–0.5° C. nearly five times better than conventional gel apparatuses. A slight side-to-side gradient was present from heat pickup as the air moved across the glass plates.

In FIG. 5c, an impingement two sided apparatus 72 has an upper buffer 73, a lower buffer 74, a glass gel slab 75, and a fan 76 that is driven by motor 77. Glass gel slab 75 is comprised of a front glass plate 78 and a back glass plate 79 which are substantially parallel to each other and between them, contain gel 80. Fan 76 is positioned below lower buffer 74. Further, fan 76 has propeller blades 81. Further, apparatus 72 also has a front impingement plate 82 that faces front 83 of front glass plate 78, and a back impingement plate 84 that faces back 85 of back glass plate 79. Both front impingement plate 82 and back impingement plate 84 have impingement holes 86. Fan 76 circulates air from beneath lower buffer 74 in a split flow manner and up along both front impingement plate 82 and back impingement plate 84 and towards upper buffer 73. The circulating air enters through impingement holes 86 and then, flows back down towards lower buffer 74. This apparatus having a common fan 76 and split flow and front and back impingement plates respectively facing the front and back glass plates provided better performance than the prototypes of FIGS. 5a and 5b. In this apparatus, the air flowing through impingement holes 86 impinge on the glass surfaces, i.e. front 83 and back 85 at substantially right angles, thereby creating local turbulence and very high heat transfer coefficients. Apparatus 72 is substantially symmetrical in that the impingement holes 86 line up along both front 83 and back 85 and the air flow is balanced by having a symmetrical design and large air distribution chambers. Apparatus 72 has walls 87 that taper as they extend from the bottom of apparatus 72 to the top of apparatus 72. This apparatus reduced the front-to-back thermal gradients across the glass plates to below 0.1° C. and at the same time provided very low side-to-side gradients of 0.3° C. Additional performance is obtained by a substantially symmetrical construction to maintain symmetrical temperature gradients in the gel 80 itself.

FIGS. 6a and 6b show another embodiment of the present invention having a turbulent-flow, two sided jet impingement apparatus 88 having front and back chambers 88' and side chambers 88". Air flow is shown with arrows. Apparatus 88 has an upper buffer 89, a lower buffer 90, a glass gel slab 91, and two scroll fans 92 powered by a single motor drive 93. Glass gel slab 91 is comprised of a front glass plate 92 and a back glass plate 93 which are substantially parallel to each other and between them, contain gel 94. Fans 92 are positioned below lower buffer 90. Further, fans 92 have propeller blades 95. Further, apparatus 88 also has a front impingement plate 96 that faces front 97 of front glass plate 92, and a back impingement plate 98 that faces back 99 of back glass plate 93. Both front impingement plate 96 and back impingement plate 98 have impingement holes 100. Air is circulated by fans 92 from below lower buffer 90 and up along and through chambers 88' and towards upper buffer 89. The circulating air enters through impingement holes 100 and then, as the air moves to side chambers 88", the air carries heat away from glass gel slab 91. The air then flows through side chambers 88" and to intake 101 of the scroll fans 92. High heat transfer is obtained by the air flowing at high velocity through the holes 100 in the impingement plates 96 and 98 at substantially right angles to the glass plates 92 and 93.

Figure 7A:
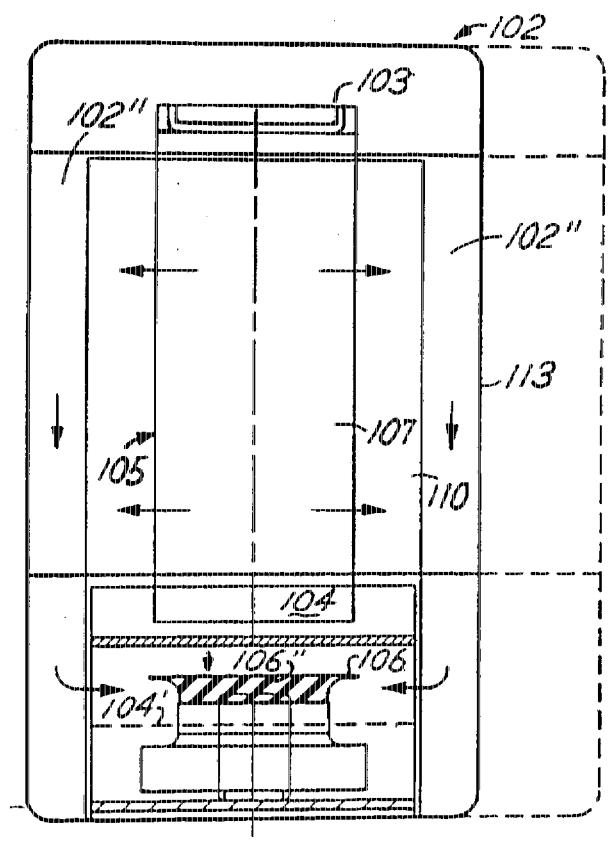
FIGS. 7a and 7b show another embodiment of the present invention having a double-sided tangential-blower jet impingement system having a single blower.
Figure 7B:
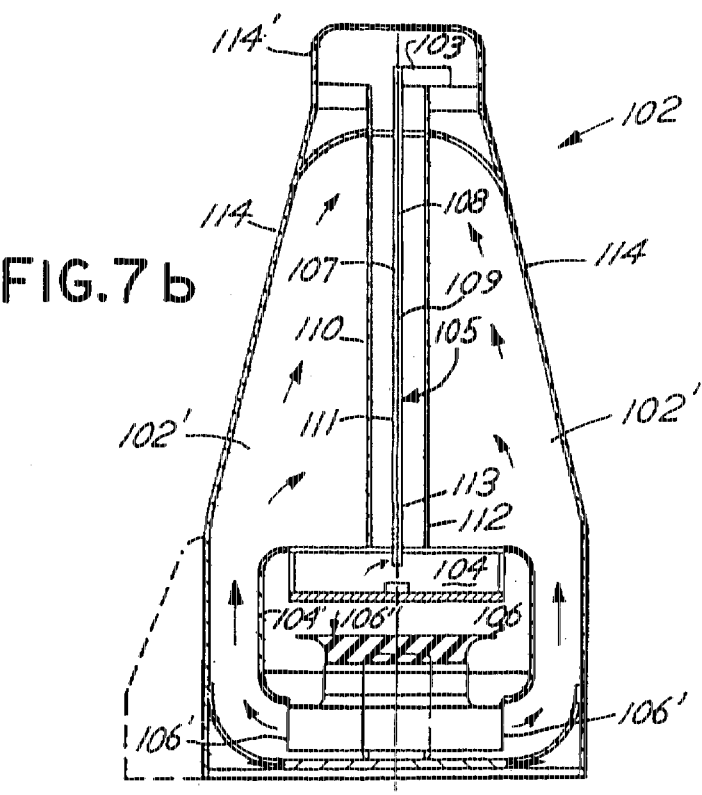

FIGS. 7a and 7b show another embodiment of the present invention having a double-sided tangential-blower jet impingement apparatus 102 having front and back chambers 102' and side chambers 102". Air flow is shown with arrows. Apparatus 102 has an upper buffer 103, a lower buffer 104, a glass gel slab 105, and a single blower fan 106 powered by a motor that is not shown. Glass gel slab 105 is comprised of a front glass plate 107 and a back glass plate 108 which are substantially parallel to each other and between them, contain gel 109. Blower fan 106 is positioned below lower buffer 104. Further, apparatus 102 also has a front impingement plate 110 that faces front 111 of front glass plate 107, and a back impingement plate 112 that faces back 113 of back glass plate 108. Both front impingement plate 110 and back impingement plate 112 have impingement holes (that are not shown but are the same as the impingement holes 100 as shown in FIGS. 6a and 6b). Air is circulated by blower fan 106 at exit 106' from below lower buffer 104 and up along and through chambers 102' and towards upper buffer 103. The circulating air enters through the impingement holes and then, as the air moves to side chambers 102", the air carries heat away from glass gel slab 105. The air then flows through side chambers 102" and to the intake 106" of blower fan 106. High heat transfer is obtained by the air flowing at high velocity through the holes in the impingement plates 110 and 112 at substantially right angles to the glass plates 107 and 108. Apparatus 102 has a barrier 104' that separates the air exiting from exit 106' and the air returning at intake 106". Apparatus 102 also has tapered walls 114 having a hinged top lid 114' that can be lifted off to allow access to the inside of apparatus 102. Apparatus 102 is similar to apparatus 88 shown in FIGS. 6a and 6b in that they both have a tangential double sided apparatus, however they are different in that instead of two scroll fans 92 as in apparatus 88, apparatus 102 has a single tangential blower fan 106.

FIGS. 8a and 8b show another embodiment of the invention having an air impingement gel temperature control apparatus 115 having front and back chambers 115' and side chambers 115". Air flow is shown with arrows. Apparatus 115 has an upper buffer 116, a lower buffer 117, a glass gel slab 118, and a blower fan 119 powered by a single motor 120. Glass gel slab 118 is comprised of a front glass plate 121 and a back glass plate 122 which are substantially parallel to each other and between them, contain gel 123. Blower fan 119 is positioned below lower buffer 117. Further, blower fan 119 has propeller blades 124. Further, apparatus 115 also has a front impingement plate 125 that faces front 126 of front glass plate 121, and a back impingement plate 127 that faces back 128 of back glass plate 122. Both front impingement plate 125 and back impingement plate 127 have impingement holes 129. Air is circulated by blower fan 119 from below lower buffer 117 and up and through chambers 115' and towards upper buffer 116. The circulating air enters through impingement holes 129 and then, as the air moves to side chambers 115", the air carries heat away from glass gel slab 118. The air then flows through side chambers 115" and to intake 130 of blower fan 119. High heat transfer is obtained by the air flowing at high velocity through the holes 100 in the impingement plates 125 and 127 at substantially right angles to the glass plates 121 and 122. Apparatus 115 has a barrier 117' that separates the air exiting from exit 124' of blower fan 119 and the air returning to the blower fan 119 at intake 130. Apparatus 115 also has mounting plates 124" for mounting the motor 120.

Figure 9A:
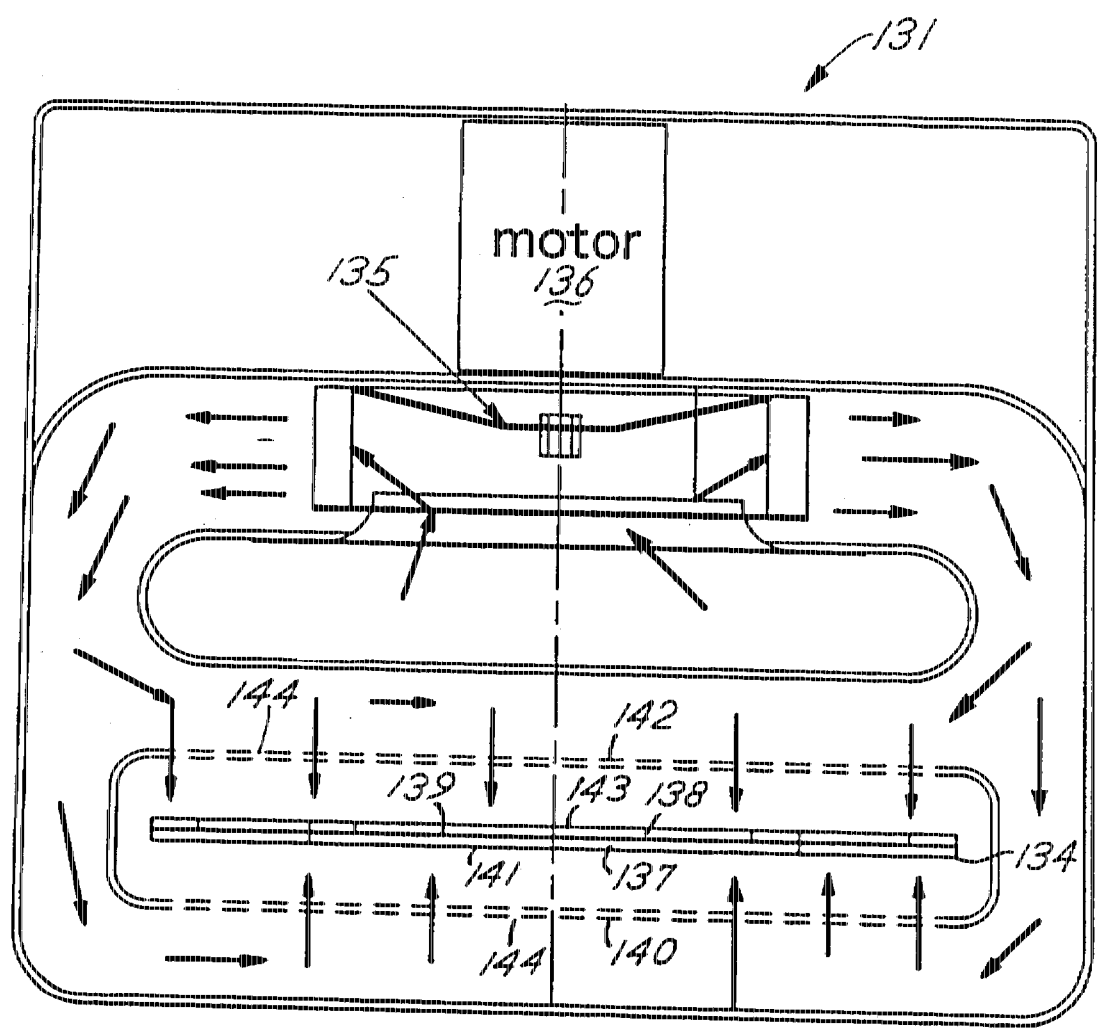
FIGS. 9a and 9b show another embodiment of the present invention having a double-sided air impingement gel temperature control apparatus having a single fan at one side of the apparatus.
Figure 9B:
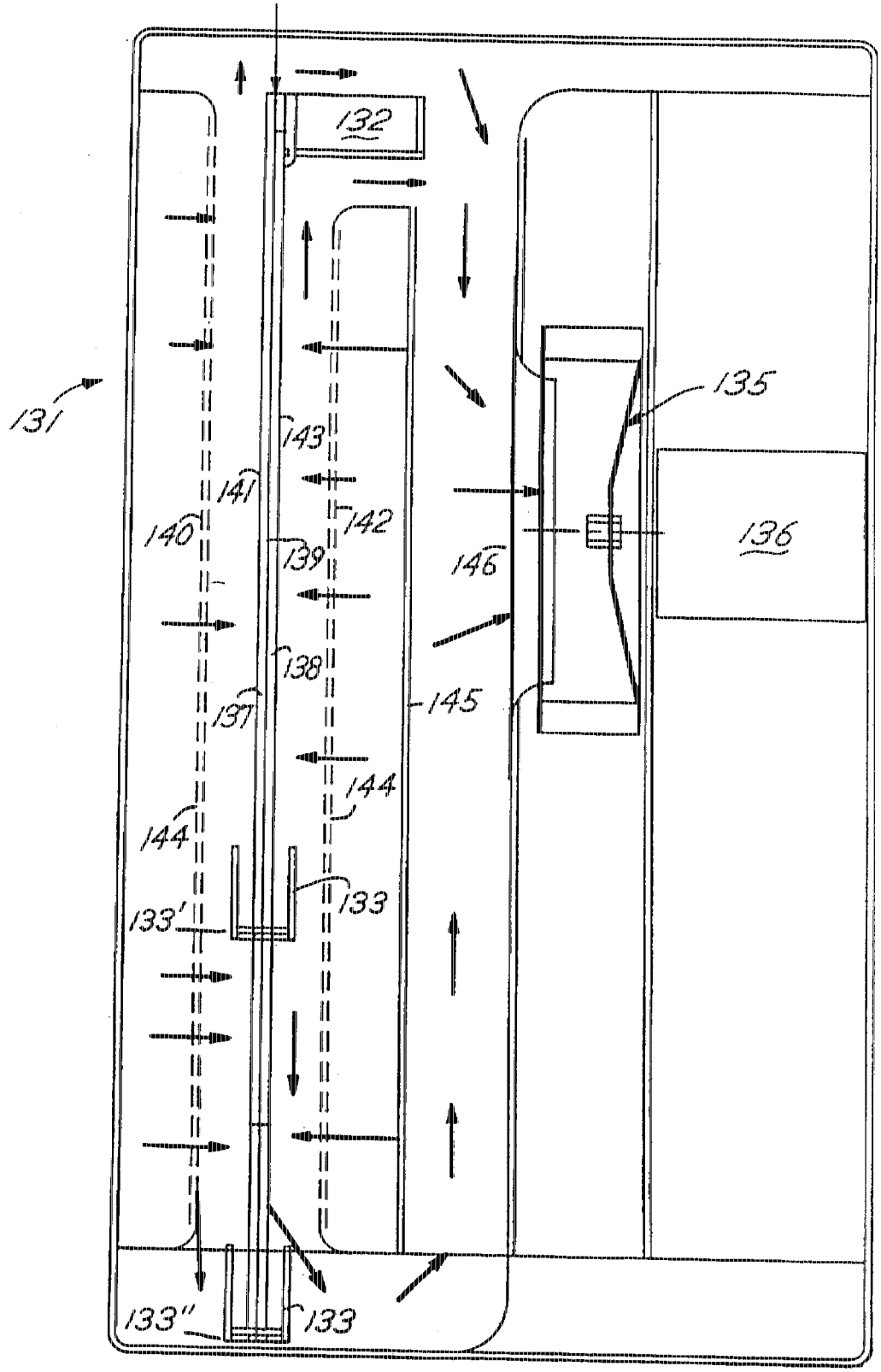

FIGS. 9a and 9b show another embodiment of the invention having an air impingement gel temperature control apparatus 131. Air flow is shown with arrows. Apparatus 131 has an upper buffer 132, a movable lower buffer 133, a glass gel slab 134, and a blower fan 135 powered by a single motor 136. Glass gel slab 134 is comprised of a front glass plate 137 and a back glass plate 138 which are substantially parallel to each other and between them, contain gel 139. Moveable lower buffer 133 can be incrementally moved toward or away from upper buffer 132 in order to accommodate various lengths of glass plates. FIG. 9b shows movable lower buffer 133 in two different positions, i.e. position 133' and position 133". In addition, apparatus 131 also has a front impingement plate 140 that faces front 141 of front glass plate 137, and a back impingement plate 142 that faces back 143 of back glass plate 138. Front impingement plate 140 and back impingement plate 142 have impingement holes 144. Apparatus 131 also has a diverter plate 145 that is positioned between blower fan 135 and back impingement plate 142. Air is circulated by blower fan 135 around diverter plate 145 in a split flow manner and around impingement plates 140 and 142. The circulating air enters through impingement holes 144 and carries heat away from glass gel slab 134. High heat transfer is obtained by the air flowing at high velocity through the holes 144 in the impingement plates 140 and 142 at substantially right angles to the glass plates 137 and 138. The air then flows along the glass plates 137 and 138, and then returns to the intake 146 of the blower fan 135. Thus, the circulating air enters through impingement holes 144 and then carries heat away from glass gel slab 134 as it flows back to intake 146 of the blower fan 135. As shown in FIG. 9b, the air can return to the blower fan 135 from the bottom and/or the top of apparatus 131. Apparatus 131 has a barrier 146' that separates the air exiting from exit 146" of blower fan 135 and the air returning to the blower fan 135 at intake 146.

Figure 10A:
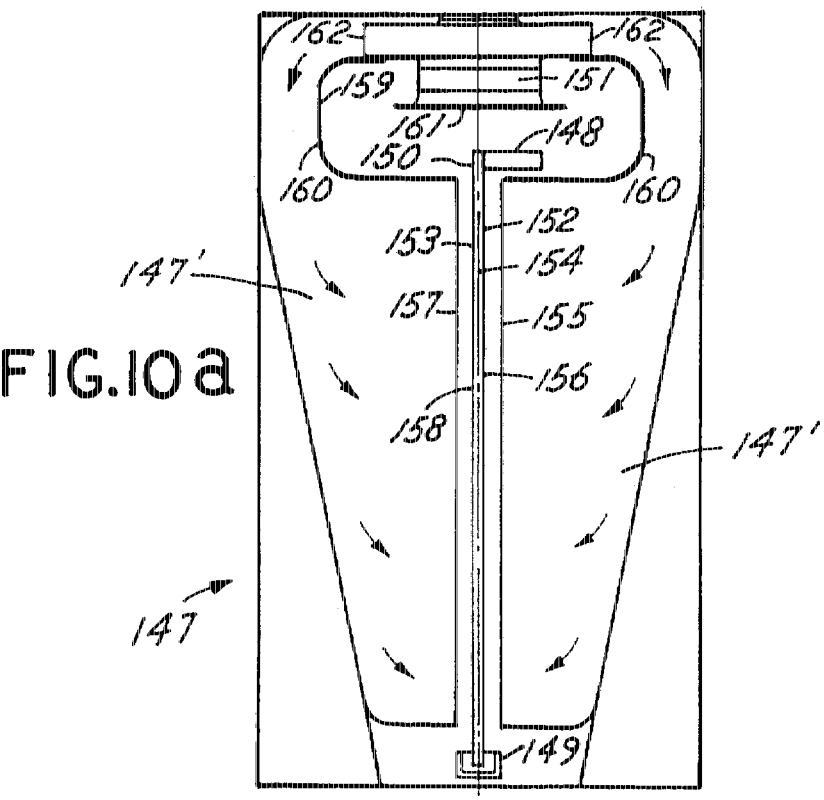
FIGS. 10a and 10b show another embodiment of the present invention having a single fan at the top of the apparatus.
Figure 10B:
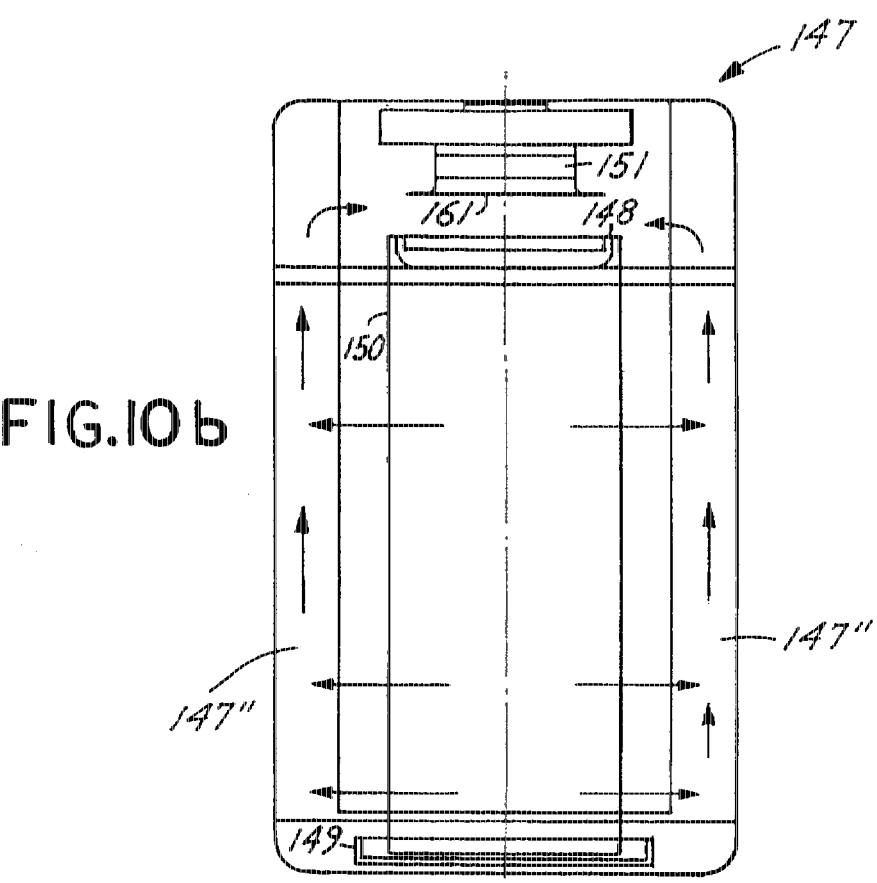

FIGS. 10a and 10b show another embodiment of the present invention having an air impingement gel temperature control apparatus 147 having front and back chambers 147' and side chambers 147". Air flow is shown with arrows. Apparatus 147 has an upper buffer 148, a lower buffer 149, a glass gel slab 150, and a blower fan 151. Glass gel slab 150 is comprised of a front glass plate 152 and a back glass plate 153 which are substantially parallel to each other and between them, contain gel 154. Blower fan 151 is positioned above upper buffer 148. Further, apparatus 147 has a front impingement plate 155 that faces front 156 of front glass plate 152, and a back impingement plate 157 that faces back 158 of back glass plate 153. Both front impingement plate 155 and back impingement plate 157 have impingement holes (that are not shown but are the same as the impingement holes 100 as shown in FIGS. 6a and 6b). Apparatus 147 also has a diverter plate 159 that is positioned around the upper buffer 148. Air is circulated by blower fan 151 around the outside surface 160 of diverter plate 159 and around impingement plates 155 and 157. The circulating air enters through impingement holes and then, as the air moves to side chambers 147", the air carries heat away from glass gel slab 150. The air then flows through side chambers 147" and to intake 161 of the blower fan 151. High heat transfer is obtained by the air flowing at high velocity through the impingement holes in the impingement plates 155 and 157 at substantially right angles to the glass plates 152 and 153. Diverter plate 159 separates the air exiting from exit 162 of blower fan 151 and the air returning to the blower fan 151 at intake 161.

The foregoing embodiments of the present invention demonstrate that there are alternative positions of the blower fan, sometimes referred to herein as a blower or fan, in relation to the rest of the apparatus. Those skilled in the art will recognize that the position of the blower fan is a design choice that may involve safety and balancing considerations. However, considering all factors, the embodiment shown in FIGS. 9a and 9b is believed to be the preferred construction.

The foregoing detailed description of the invention has been made in general terms and with respect to several preferred embodiments. Many of the preferred apparatuses and methods stated herein may be varied by persons skilled in the art without departing from the spirit and scope of the present invention as set forth in the following claims and equivalents.

What is claimed is:

1. A gel electrophoresis separation apparatus for controlling the temperature gradients of an electrophoresis gel during electrophoresis, comprising, in combination:

a gaseous heat-exchange medium driving means, and an impingement means comprising a front impingement plate and a back impingement plate, each with a plurality of openings, whereby a gaseous heat-exchange medium is driven by the gaseous heat-exchange medium driving means through the openings to create turbulent gas flow, on the surface of gel electrophoresis plates, whereby the turbulent has flow induced by passage of the gaseous heat-exchange medium through the openings of the impingement means minimizes temperature gradients within the electrophoresis gel contained by the gel electrophoresis plates.

2. The apparatus of claim 1, wherein the gaseous heat-exchange medium driving means comprises a blower.

3. The apparatus of claim 1, wherein the gaseous heat-exchange medium is air and the gaseous heat-exchange medium driving means comprises a fan.

4. A gel electrophoresis separation apparatus for controlling the temperature gradients of an electrophoresis gel during electrophoresis, the improvement comprising:

a temperature control assembly, comprising a gaseous heat-exchange medium containment means arranged to define a gaseous heat-exchange medium volume, a gaseous heat-exchange medium driving means, and an impingement means, comprising a front impingement plate and a back impingement plate, each having a plurality of openings, whereby a gaseous heat-exchange medium is driven by the gaseous heat-exchange medium driving means within the gaseous heat-exchange medium containment volume and through the openings of the impingement means, causing turbulent gas flow of the gaseous heat-exchange medium within and adjacent to the electrophoresis gel, the turbulent gas flow induced by passage of the gaseous heat-exchange medium through the openings of the impingement means thereby minimizing temperature gradients within the electrophoresis gel.

5. The gel electrophoresis separation apparatus according to claim 4, wherein the impingement means comprises a first impingement plate and a second impingement plate;

the impingement plates being approximately equal in size and substantially rectangular, each plate having an inner face and an outer face and a plurality of throughbores; the faces of each impingement plate being oriented approximately parallel to each other; the throughbores disposed approximately perpendicularly to the impingement plate faces and thereby defining impingement passageways;

whereby the first impingement plate is located adjacent to a first gel plate of the gel electrophoresis separation apparatus and arranged to substantially cover it, and defining a space between the gel plate and the impingement plate;

the second impingement plate is located adjacent to a second gel plate of the gel electrophoresis separation apparatus and arranged to substantially cover it, and defining a space between the gel plate and the impingement plate, wherein the first and second gel plates define a gel-containing region located between the gel plates.

6. The gel electrophoresis separation apparatus according to claim 5, wherein the impingement plates and the gel plates are each of approximately equal rectangular cross-sectional area.

7. The gel electrophoresis separation apparatus according to claim 4, wherein the gaseous heat-exchange medium driving means comprises a blower.

8. The gel electrophoresis separation apparatus according to claim 4, wherein the gaseous heat-exchange medium is air and the gaseous heat-exchange medium driving means comprises a fan.

9. A gel electrophoresis separation apparatus, the improvement comprising:

a temperature control assembly, comprising a volume of a gaseous heat-exchange medium, a gaseous heat-exchange medium containment housing arranged to define a gaseous heat-exchange medium volume having an outer periphery, a first gaseous heat-exchange medium containment region, a second gaseous heat-exchange medium containment region distal to the first region and separated from the first region by a central gaseous heat-exchange medium containment region; means for driving a gaseous heat-exchange medium within the gaseous heat-exchange medium containment volume wherein the gaseous heat-exchange medium driving means is arranged proximally to the second gaseous heat-exchange medium containment region;

means for directing the gaseous heat-exchange medium to flow along the outer periphery of the gaseous heat-exchange medium containment volume; and a first and a second impingement plate;

the impingement plates being approximately equal in size and substantially rectangular, each plate having an inner face and a plurality of throughbores; the faces of each impingement plate being oriented approximately parallel to each other; the throughbores disposed approximately perpendicularly to the impingement plate faces and thereby defining impingement passageways;

whereby the first impingement plate is located adjacent to a first gel plate of the gel electrophoresis separation apparatus and arranged to substantially cover it, and defining a space between the gel plate and the impingement plate;

the second impingement plate is located adjacent to a second gel plate of the gel electrophoresis separation apparatus and arranged to substantially cover it, and defining a space between the gel plate and the impingement plate, wherein the first and second gel plates define a gel-containing region located between the first and second gel plates;

whereby the gaseous heat-exchange medium is driven by the gaseous heat-exchange medium driving means within the gaseous heat-exchange medium containment volume along the periphery towards the first region distal to the driving means, and thereby moving through the central region and being contacted with the outer faces of the impingement plates, whereby the gaseous heat-exchange medium communicates with the plurality of throughbores of each of the impingement plates, causing turbulent flow of the gaseous heat-exchange medium within and into the spaces between the gel plates and the impingement plates, and thereby moving to the second region proximal to the gaseous heat-exchange medium driving means;

the turbulent flow induced by passage of the gaseous heat-exchange medium through the throughbores of the impingement plates thereby minimizing temperature gradients within the gel-containing region between the gel plates.

10. A gel electrophoresis separation apparatus according to claim 9, wherein the impingement plates and the gel plates are each of approximately equal rectangular cross-sectional area.

11. A gel electrophoresis separation apparatus according to claim 9, wherein the impingement plates are approximately identical in dimension.

12. A gel electrophoresis separation apparatus according to claim 9, wherein the gel plates are positioned approximately centrally within the gaseous heat-exchange medium containment housing, thereby bisecting the gaseous heat-exchange medium containment volume.

13. A gel electrophoresis separation apparatus according to claim 9, wherein the gaseous heat-exchange medium driving means comprises a blower.

14. A gel electrophoresis separation apparatus according to claim 9, wherein the means for directing the gaseous heat-exchange medium to flow along the outer periphery of the gaseous heat-exchange medium containment volume comprises a cap shroud.

15. A gel electrophoresis separation apparatus according to claim 14, wherein the cap shroud is located in the gaseous heat-exchange medium containment region proximal to the gaseous heat-exchange medium driving means.

16. A gel electrophoresis separation apparatus according to claim 9, wherein the gaseous heat-exchange medium is air and the gaseous heat-exchange medium driving means comprises a fan.

17. A gel electrophoresis separation apparatus having, in combination:

a first gel plate, a second gel plate, a first buffer reservoir, a second buffer reservoir and a temperature control subassembly;

the first gel plate and the second gel plate being approximately equal in size and substantially rectangular, the gel plates being oriented substantially parallel to one another and defining a gel-containing region, the gel plates each having an inner, gel-contacting face and an outer face, and a first edge, a pair of side edges, and a second edge, wherein the gel-containing region is further defined by a pair of spacers located between the first and second plates substantially along each of the side edges;

the first buffer reservoir being adjacent to the first edge and communicating with the gel-containing region;

the second buffer reservoir being adjacent to the second edge and communicating with the gel-containing region;

the temperature control assembly further having a gaseous heat-exchange medium containment housing arranged to define a gaseous heat-exchange medium volume having an outer periphery, a first gaseous heat-exchange medium containment region, a second gaseous heat-exchange medium containment region distal to the first region and separated from the first region by a central gaseous heat-exchange medium containment region; means for driving a gaseous heat-exchange medium within the gaseous heat-exchange medium containment volume wherein the gaseous heat-exchange medium driving means is arranged proximally to the second gaseous heat-exchange medium containment region; means for directing the gaseous heat-exchange medium to flow along the outer periphery of the gaseous heat-exchange medium containment volume; and a first impingement plate and a second impingement plate;

the impingement plates being approximately equal in size and substantially rectangular, each plate having an inner face and an outer face and a plurality of throughbores; the faces of each impingement plate being oriented approximately parallel to each other; the throughbores disposed approximately perpendicularly to the impingement plate faces and thereby defining impingement passageways;

the first impingement plate being located adjacent to the first gel plate and arranged to substantially cover it, and defining a space between the gel plate and the impingement plate;

the second impingement plate being located adjacent to the second gel plate and arranged to substantially cover it, and defining a space between the gel plate and the impingement plate; whereby the gaseous heat-exchange medium is driven by the gaseous heat-exchange medium driving means within the gaseous heat-exchange medium containment volume along the periphery of the gaseous heat-exchange medium containment housing towards the first region distal to the driving means, and thereby moving through the central region and being contacted with the outer faces of the impingement plates, whereby the gaseous heat-exchange medium communicates with the plurality of throughbores of each of the impingement plates, causing turbulent flow of the gaseous heat-exchange medium within and into the spaces between the gel plates and the impingement plates, and thereby moving to the second region proximal to the gaseous heat-exchange medium driving means;

the turbulent flow induced by passage of the gaseous heat-exchange medium through the throughbores of the impingement plates thereby minimizing temperature gradients within the gel-containing region between the gel plates.

18. A gel electrophoresis separation apparatus according to claim 17, wherein the impingement plates and the gel plates are each of approximately equal rectangular cross-sectional area.

19. A gel electrophoresis separation apparatus according to claim 17, wherein the impingement plates are approximately identical in dimension.

20. A gel electrophoresis separation apparatus according to claim 17, wherein the gel plates are positioned approximately centrally within the gaseous heat-exchange medium containment housing, thereby bisecting the gaseous heat-exchange medium containment volume.

21. A gel electrophoresis separation apparatus according to claim 17, wherein the gaseous heat-exchange medium driving means comprises a blower.

22. A gel electrophoresis separation apparatus according to claim 21, wherein the blower is located proximally to either the first or second edge of the gel plates.

23. A gel electrophoresis separation apparatus according to claim 17, wherein the means for directing the gaseous heat-exchange medium to flow along the outer periphery of the gaseous heat-exchange medium containment volume comprises a cap shroud.

24. A gel electrophoresis separation apparatus according to claim 23, wherein the cap shroud is located in the gaseous heat-exchange medium containment region proximal to the gaseous heat-exchange medium driving means.

25. A gel electrophoresis separation apparatus according to claim 17, wherein the gaseous heat-exchange medium is air and the gaseous heat-exchange medium driving means comprises a fan.

26. A gel electrophoresis separation apparatus according to claim 25, wherein the fan is located proximally either the first or second edge of the gel plates.

27. A gel electrophoresis separation apparatus according to claim 17, wherein the gaseous heat-exchange medium containment housing comprises side panels having a length and separated by a distance, wherein the side panels are arranged so that the distance between the side panels increases along the length of the panels, and wherein the arrangement of the side panels subtends an angle between the panels, said angle being from about 10 degrees to about 90 degrees, whereby the cross-sectional area of the volume defined by the containment housing is smaller in the first gaseous heat-exchange medium containment region than in the second gaseous heat-exchange medium containment region.

28. A gel electrophoresis separation apparatus according to claim 17, wherein the gas heat-exchange medium driving means is oriented substantially perpendicularly to either the first or the second edge of the gel plates.

29. A gel electrophoresis separation apparatus according to claim 17, wherein the first and the second buffer reservoirs are physically isolated from the gas heat-exchange medium containment volume.

30. A gel electrophoresis separation apparatus according to claim 17, wherein gel electrophoresis separation is performed at a temperature greater than ambient temperature.

31. In a slab gel electrophoresis separation apparatus, wherein electrophoresis is conducted in a slab gel between a first and second plate in an enclosed controlled-environment chamber having a first and second wall respectively opposite the first and second gel plate, an improvement comprising a first impingement means located between the first gel plate and the first wall and a second impingement means located between the second gel plate and the second wall wherein each impingement means defines a plurality of openings, in combination with a means for generating a stream of a gaseous heat-exchange medium between the first and second impingement means and the first and second walls wherein the gaseous heat-exchange medium passes through the openings in the first and second impingement means to perpendicularly impinge the gaseous heat-exchange medium on the first and second gel plates and thereby provide a uniform temperature in the slab gel during electrophoresis.

* * * * *